United States Patent [19]
Peterson

[11] Patent Number: 5,925,833
[45] Date of Patent: Jul. 20, 1999

[54] PROCESS PLANT SAMPLE COLLECTION SYSTEM AND METHOD

[76] Inventor: Roger Peterson, 375 Country Rd., Old Ocean, Tex. 77463

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/797,479

[22] Filed: Mar. 24, 1997

[51] Int. Cl.⁶ ........................................................ G01N 1/20
[52] U.S. Cl. ................................... 73/863.72; 73/863.57
[58] Field of Search ........................... 73/863.72, 863.71, 73/863.73, 863.81, 863.86, 863.02

[56] References Cited

U.S. PATENT DOCUMENTS

| | | | |
|---|---|---|---|
| 2,864,254 | 12/1958 | McDonald et al. | 73/863.73 |
| 4,133,642 | 1/1979 | Nosaka et al. | 73/864.91 |
| 4,195,525 | 4/1980 | George et al. | 73/863.73 |
| 4,209,585 | 6/1980 | Lloyd et al. | 435/30 |
| 4,887,472 | 12/1989 | Jansen | 73/863.86 |
| 4,974,457 | 12/1990 | Angst et al. | 73/863.81 |
| 5,265,483 | 11/1993 | Farrell et al. | 73/863.73 |
| 5,345,828 | 9/1994 | Peterson | 73/863.72 |
| 5,600,075 | 2/1997 | Peterson | 73/863.71 |
| 5,652,398 | 7/1997 | Johnson | 73/863.71 |

*Primary Examiner*—Hezron Williams
*Assistant Examiner*—Chad Soliz
*Attorney, Agent, or Firm*—Gunn & Associates, P.C.

[57] ABSTRACT

This disclosure sets out a method and apparatus for extracting repeated process samples. Each sample is put into a segregated bottle or container and the container is dated and time stamped. The containers are arranged in sequence on a feed system and are filled in sequence and marked.

12 Claims, 4 Drawing Sheets

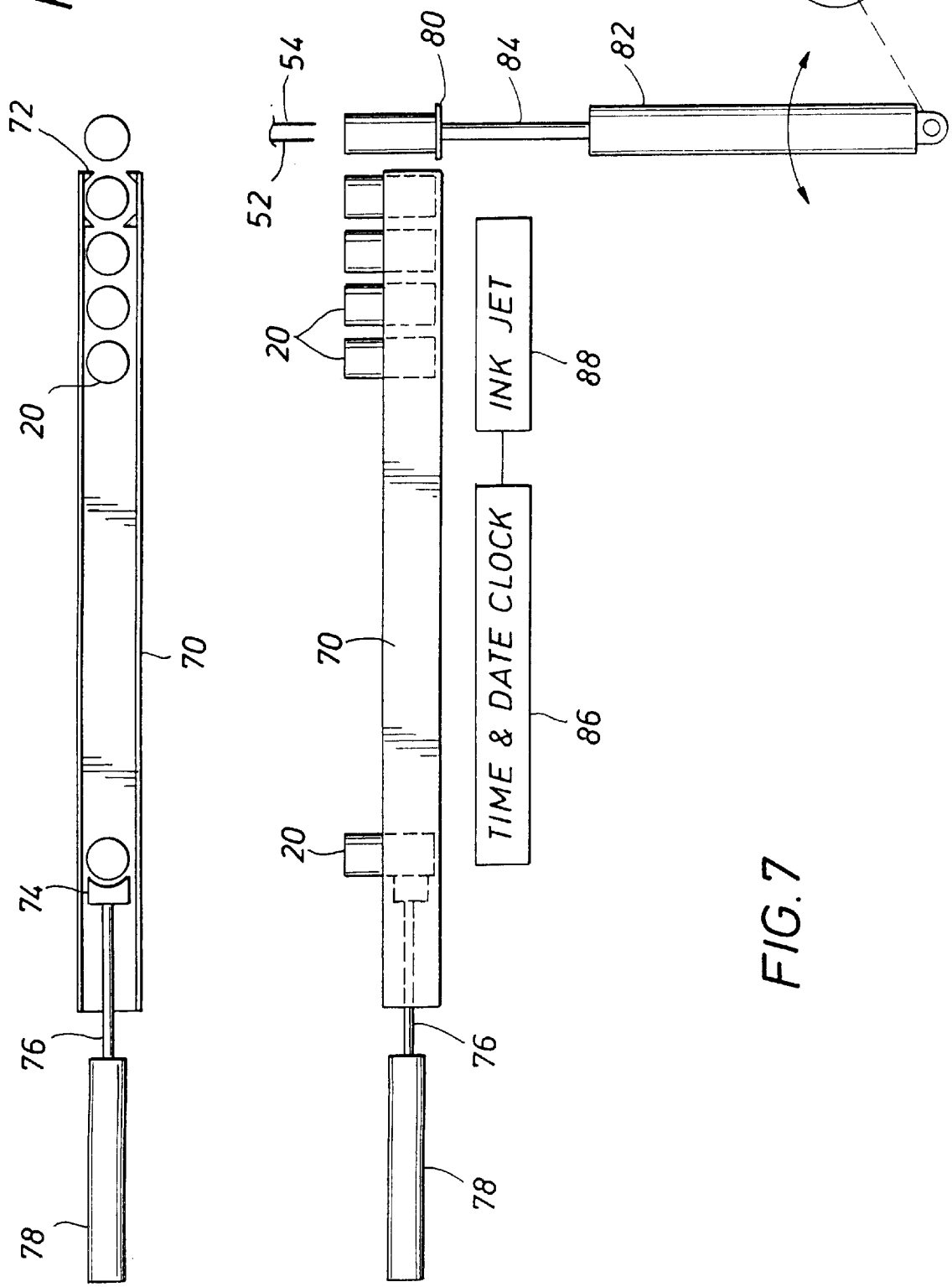

PROCESS PLANT SAMPLE COLLECTION SYSTEM AND METHOD

BACKGROUND OF THE DISCLOSURE

Consider the testing of a chemical processing plant which is placed on line and operates indefinitely. Periodically, it is necessary to test the product made in the plant. That is a difficult task to accomplish in many circumstances, especially those where the process operates at very high pressures and temperatures. Typically, high pressures and temperatures making it difficult to obtain a sample. Moreover, expensive metals and expensive fabrication techniques are required to enable the processing plant to be properly confined within the structure which holds the process. This remains a problem even when only a small sample is required for periodic testing. Not only must the sample be removed from the process plant, the sample must be delivered into a sample container for easy transportation to a lab for testing. Consider as an example a petrochemical processing plant where a process is carried out at elevated temperatures of over 1000° F. and very high pressures limited primarily by the pressure rating of the equipment of the sample collection system. The fluid flowing in the process pipes and pressure vessels of the processing plant may flow at a rate of hundreds of gallons per minute, and yet only a small portion is required for testing, for example, one liter.

There is even the possibility that the sample will change from a gas to liquid on reducing the temperature and pressure while removing the sample. Transfer of the sample from the interior of a process plant through the walls of the pipes or other pressure vessels which contain the process requires tapping the process to obtain the sample, and this must be done without permitting the sample to escape to atmosphere. Except in rare cases, such a sample is at least partially, and often extremely volatile. In any event, a sample must be removed from the processing plant, transferred through a set of flow lines, metered into some sort of sample container, and then delivered for subsequent testing, for instance, at a testing laboratory sample analysis or other testing can be carried out. One mode of testing is to fill a small sample container, carry it to the testing lab, and conduct the test there. This enables a single testing lab to test samples from several different locations on a process plant. For instance, a single process plant may comprise several different columns with intermediate stages of processing, thereby generating samples at 10 or 20 different locations; samples are obtained at different times of the day from the several sample locations, the tests are then run, and product quality and purity is then certified as a result of the laboratory testing.

The present apparatus and method enable periodic testing to be carried out in this fashion. This disclosure sets forth a means and mechanism for such testing notwithstanding the fact that testing is required of the product when the product is manufactured at extremely high pressures and temperatures. There is a problem in transfer of the sample. For instance, as a result of high process temperatures, the removed product typically will be a gas, and will tend to be reduced in size should it undergo a phase of conversion from gas to liquid. On the other hand, because of extremely high pressures, a sample will tend to expand when the pressure confinement is reduced. It is therefore somewhat difficult to scale the amount of sample to be removed so that the proper size and consistent size of sample can be provided in a sample container. The present apparatus enables this to be accomplished. Moreover, it is accomplished in the context where one or several sample containers are serially filled with each separated from the other at the sample taking device. The timed separation of samples is accomplished by providing fixed flow lines extending to the sample receiving container which are periodically purged with nitrogen to assure that there is no remnant of sample gas in the lines for later sample collection. The purging of lines assures that two samples taken hours apart are not mixed serially by storage in the connective lines. Moreover, this is all accomplished without permitting fugitive emissions to atmosphere. In part, that is prevented and protected against by utilization of a closed housing which is maintained under a blanket of nitrogen. This assures that there will be minimal accumulation of explosive gases in the housing, or gases which otherwise create some type of hazard. Finally, the system operates so that it can be cyclically controlled by a handle for the purpose of periodic operation of a two position, six port valve. In another form, operation is by a motor and timer. A sample taking system may be operated periodically to obtain or remove a sample from a system. One aspect of the present invention is the provision of a small sample measuring loop connected to a six port valve. A small loop is a storage container. It is however relatively small. It stores a specified quantity of the sample. One suitable quantity of sample is one cubic centimeter. This is normally written as one cc. It is possible to connect a sample storage loop of this limited capacity to a six port, two way valve. That is, the sample storage loop serves a meter device to assure that the sample is sized to the size required. In addition to that, the present disclosure sets forth a sample container system which can be adapted for receipt of a measured small sample. Assume for purposes of discussion that a sample is required once per hour. By using a larger container, twenty-four samples taken in a single day can be stored in the container. They are mixed or blended. That may for sufficient to laboratory testing to provide an assay later. On the other hand, the sample may require uniquely separate treating and testing. For example, this can occur in the instance that a small sample is taken and the small sample is put into a container and not mixed with any other sample. In that instance, the sample container should be sized to the same size or one cubic centimeter.

The present disclosure sets forth a system which provides such a sample mechanism. The sample mechanism in this instance is provided with a procession of single sample containers which are scaled so that the volume of the container matches the volume in the sample loop. In the example just mentioned, one cc of samples obtained and stored in a container which has a capacity of one cc. Perhaps, there will be a modest amount of head room in the sample container beneath the covered mouth and septum over the mouth of the container. In that instance, one sample can be taken per hour and twenty four different containers will be filled. Each of the several containers is filled in the described manner. Each container is provided with this measured amount.

The measured volume introduced into the container is received into the container and stored so that spillage or commingling is avoided. In the example given, to obtain one sample per hour, twenty four separate containers are required. The present disclosure provides an indexing mechanism which aligns a series of containers for syringe filling. Each is filled individually. A mechanism is further disclosed which labels each of the containers. Typically, the containers look alike and bear similar markings on exterior. They are filled with the same fluid although the fluid may differ from moment to moment as a result to changes in the operating process. For sample taking purposes and to have an acceptable assay of the separate samples, it is necessary to label the individual containers. That is done in the present disclosure by a label printing mechanism. To the extent that the system operates with several different containers, each is labeled so that they can be individually tested at a remote laboratory either in sequence or in any mixed sequence. The results are nevertheless readily able to be isolated to a particular time of day. This may tell much about the operation of the plan. In one example, the plant may be susceptible to sun load. At the night the plant operating characteristics might change because the sun load is reduced. This could produce a different product purity, perhaps differing only slightly, but perhaps differing substantially. It is possible for the product to be sufficiently out of the required specifications for that product stream that the product is momentarily substandard. The product can be produced in such a fashion to be exceedingly rich, and thereby unduly expensive. That is just as great a problem as being substandard.

In summary, the present disclosure is a system for transfer of a sample by means of permanently made connections to a process across a flow restriction in the process. Connection is through an inlet line and outlet line. These connections extend to two ports on a six port valve. There is a sample storage loop in the six port valve. The sample storage loop includes a sized volumetric buffer tank or sample line. It is sized so that the sample that is delivered at the prevailing pressure and temperature is held in this buffer tank. To the extent that there is either expansion or contraction by transfer out of the process plant to a reduced pressure and a temperature approaching ambient, there is sufficient size in the buffer tank to permit a properly sized sample to be collected. The tank can be large or small. A purge gas source connected to a needle valve with a flow meter connects to a fifth port, and the sixth valve port is connected by means of a sample line extending to a syringe needle for filling a closed sample container. A sequence of operations is also set forth where the sample is delivered for intermediate holding and later for delivery into the sample receiving container. In addition to that, the equipment operates in a sequence to direct a continuous flow of nitrogen for purging of the connective lines. The sample from the system can be collected in a large container holding several samples (e.g., samples from one day of operation) or can be stored in a small container sized to store one small sample. In this instance, sample containers are marked as they are serially sequentially filled.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 7 is a side view of a magazine loading mechanism which delivers a number of individual sample holding containers serially along a trough which positions the sample containers beneath a pair of syringes for filling wherein individual sample containers are filled and subsequently numbered with a suitable code number and dumped into a storage container; and FIG. 8 is a plan view of the trough shown in FIG. 7 further showing details of a detent mechanism so that only one sample container is supplied for each operation.

DETAILED DESCRIPTION OF THE PREFERRED EMBODIMENT

Figure 1:
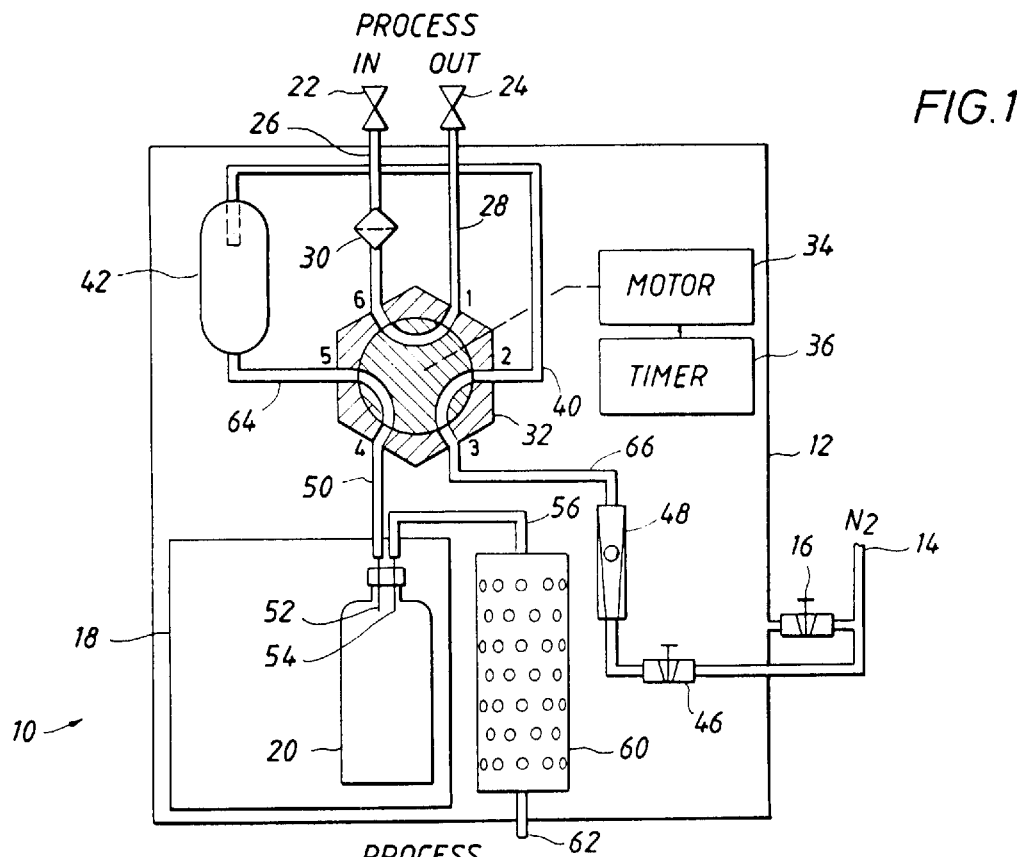
FIG. 1 is a schematic of the sample collecting apparatus of the present disclosure showing a system where the material to be sampled flows through the circulate pathway and is returned by the process and the buffer tank is empty while a nitrogen purge occurs.

In the drawings, the numeral 10 identifies the sample collection apparatus of the present disclosure. This apparatus is constructed within a cabinet 12 which comprises a closed housing. Preferably, it is made of sheet metal, but in many instances, it can be an explosion proof housing or cabinet. To increase and enhance the safety of the system it may be helpful dependent on the type of material being sampled to fill this housing with a blanket of nitrogen. A nitrogen source 14 provides a flow of nitrogen through a feed which in turn connects with a needle valve 16, the needle valve being input to the housing 12 to fill the interior with nitrogen. It is desirable to do this in instances where the material being tested tends to form an explosive mixture with air, or perhaps poses some other threat. The remainder of the equipment is preferably located in the housing 12. Conveniently, the housing 12 can be provided with an optional door. The door 18 permits operator handling of the sample receiving container 20 which is installed for holding of a measured sample. Typically, the container 20 is sized to a particular size such as one liter. Typically, it is a closed vessel which is covered over with a cap at the narrow neck or throat of the container. The cap has a hold provided in it large enough to receive the sampling needles and captures a rubber/Teflon laminated sheet of material functioning as a septum. The septum is a healing membrane which is punctured but does not leak.

Operation of the system will be described in detail after reviewing the apparatus involved in the present disclosure. To this end, there is a valve 22 which is connected with some aspect of a manufacturing process such as in a distillation column, cat cracker and the like. The valve 22 is spaced from a similar valve 24. They are located so that there is some small pressure drop between the two. This enables the inlet line 26 to receive a flow of the process fluid. The inlet line 26 is similar to the outlet line 28 which returns surplus fluid to the process. In a typical circumstance, the pressure in the lines 26 and 28 is substantially the same, and can be easily as high as 500 psi but there is a differential of about 5 or 10 psi. Higher pressures can be handled by heavy duty equipment.

A filter 30 is serially connected in the inlet valve 26. In turn, then line 26 also connects with a two position, six port valve 32. The valve has a valve body with a rotor on the interior which is rotated typically by 60° at the urging of a motor 34 connected to the rotor. The motor is periodically operated by a timer 36 to rotate by 60°. This changes the alignment of the ports as will be observed in contrasting FIG. 1 and FIG. 2 of the drawings. Hand operation of the valve is also possible.

The system has other connections to the valve 32. The numeral 40 identifies a line which loops from one port to another report on the valve 32 and serially connects with a buffer tank 42. The tank 42 is an intermediate location which holds the desired quantity of sample. More will be noted regarding the purpose of this intermediate holding step, and especially the amount held at that location.

The nitrogen supply 14 connects through an adjustable needle valve 46 which serially introduces nitrogen flow through a flow meter 48. The flow meter 48 is preferably mounted so that it can be viewed. This assures the operator that nitrogen gas is flowing into the system for purging of the lines as will be described. Another connection to the valve is provided by the sample line 50 which is terminated at a syringe needle 52. That needle introduces sample into the storage container 20. The storage container 20 also provides an outlet for gas in the bottle 20 which is removed through a similar syringe needle 54, flowing in a line 56, and then, in the form of waste products, is delivered through a filter system 60 and vented to atmosphere. The filter 60 is packed with a material which absorbs and purifies the discharge so that the discharged atmosphere is substantially inert, meaning primarily nitrogen gas flow through an atmospheric discharge passage 62. If desired, the outlet 62 can be connected with a flare in the event that the material can be combusted readily.

DETAILED DESCRIPTION OF THE METHOD OF FILLING AND PURGING

Figure 2:
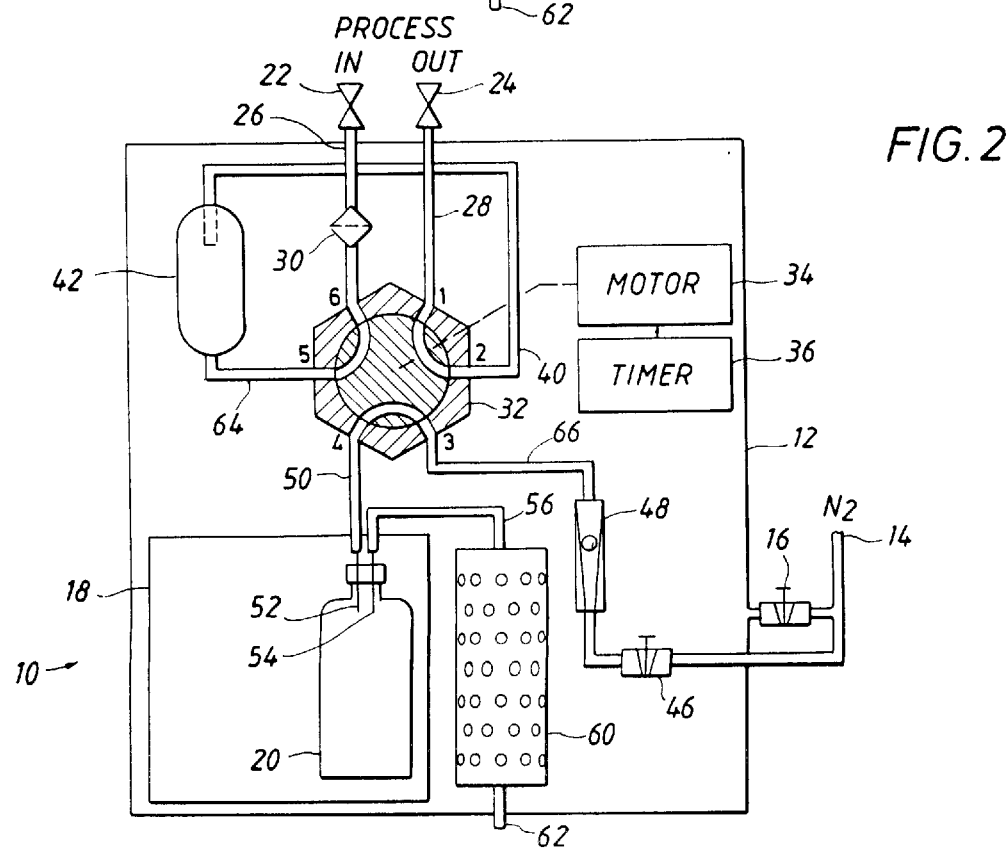
FIG. 2 of the drawings shows the system of FIG. 1 after switching so that connections are altered for filling the buffer tank which is a sequential step in comparison with the arrangement shown in FIG. 1 of the drawings.
Figure 3:
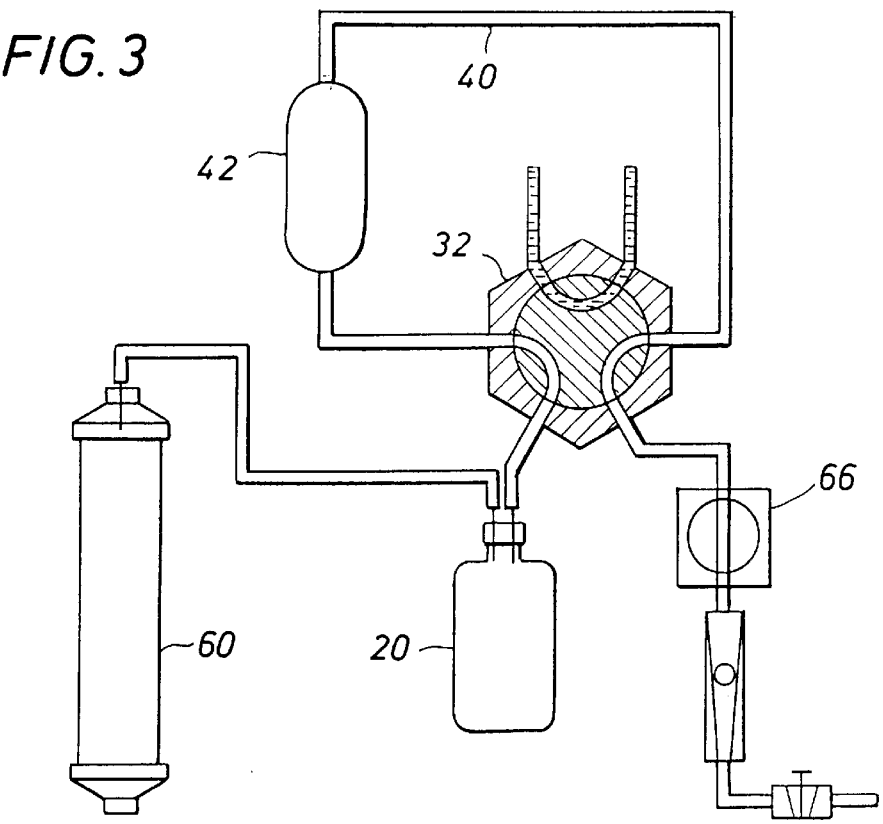
FIGS. 3–6 sequentially show different steps involved in filling a sample container including the steps of purging the storage loop and sample container in FIG. 3, filling the sample loop in FIG. 4 while continuing to purge, emptying the sample loop with purge gas to fill the sample container, and then blocking flow so the sample container can be removed, the sample loop purged, and discharging any surplus of the specimen through the filter.

Attention is now directed to FIG. 2 of the drawings for a description of a filling and purging sequence. This description will particularly focus on those things which occur when the raw sample is being obtained from the process plant In FIG. 2 of the drawings, the valve 32 is positioned so that there is a flow path in the following sequence, namely process fluid is delivered through the inlet line 26, flowing into a line 64, the buffer tank 42, the line 40 and back through the valve 32 and to the outlet line 28. As an example, assume that this position of the equipment is maintained for a few minutes so that the process fluid circulates several times through this route. After this, time assures that all the lines and especially the buffer tank 42 are filled with the process fluid, and that is accomplished without dilution. Recalling that the process fluid may be at several hundred psi pressure, and elevated temperature, there is a connection of any needed short or long distance to the present system. Whatever the case, and assuming a requisite interval for circulation in the connected lines just described, the valve 32 is operated from the position shown in FIG. 2 to the position shown in FIG. 1. The position in FIG. 1 will be described as the filling position. Filling focuses primarily on filling the container 42. In the filling position shown in FIG. 2, there is sufficient pressure differential to cause continued flow along the path described. There may however be a phase change dependent on the cooling interval after switching the valve 32 from the position shown in FIG. 2 of the drawings to the postiion shown in FIG. 1. This movement positions the valve so that there is a completley different arrangement of the connections through the valve and that will be described as the sampling position. The sampling position occurs in the following fashion. The timer 36 in conjunction with the motor 34 moves the valve by 60°. This breaks the connection which was accomplished in the loop 40, and completely reconnects the loop 40. This new flow sequence will then be described beginning with the nitrogen source 14. Nitrogen is delivered ratably through the needle valve 46, through the flow regulator 48, and the line 66. The nitrogen flows through the valve 32 and into the sample loop 40 into the buffer tank 42. Fluid continues to flow through the line 64 back through the valve 32, the line 50 and the syringe 52 for filling the sample receiving container 20. In brief, the nitrogen is delivered at a flow rate and for an interval sufficient to force the atmosphere that was initially in the container 20 out of the container. The container 20 is voided through the filter 60. Moreover, this nitrogen flow path continues to operate so that a sufficient quantity of the sample is forced from the buffer tank 42 along the flow path into the removable sample receiving container 20 to file it to a desirable level. Vapors contained within the container 20 are forced out through the filter but that does not pose a problem with fugitive emissions as a result of the filter operation.

Operator attendance is involved in the present apparatus by removal of a filled sample container 20 and replacement of it with an empty sample container. If a sample is taken every day, then the container 20 is removed daily and replaced. Removal requires pulling the sample container 20 downwardly so that the two syringe needles retract from the septum. This seals the interior. A new sample container is installed by removal of the metal cap over the septum, and pushing the container 20 upwardly so that the two needles are inserted through the septum for filling. This periodic removal and replacement assures that individual samples can be taken at the requisite interval, removed from the area and taken to a test lab, and yet the equipment is left in a condition so that another sample can be collected.

FIGS. 3–6

Jointly, FIGS. 3–6 show a sequence of operations using the device of FIG. 1. In this instance, it has been enhanced by the incorporation of a blocking valve 66 which functions in a manner to be described. To understand the sequence of operation, the valve 32 has been operated so that process fluid circulates but is not sampled. Rather, the purged gas (normally nitrogen in most instances) is delivered in the ordinary fashion, and flows through the valve 32 because the blocking valve 66 is opened. This flow of purge gas is delivered to the sample storage loop 40. This includes the tank 42. However, an alternate size can be used including sizes sufficiently larger if the sample is one liter or bigger, or is so small that the sample is only about one cc, or even smaller if desired. In any case, this part of the system is purged by delivery of the purge gas to clear the lines to assure that the process equipment lines do not bias the test data from remnants of a prior test left in the system.

Figure 4:
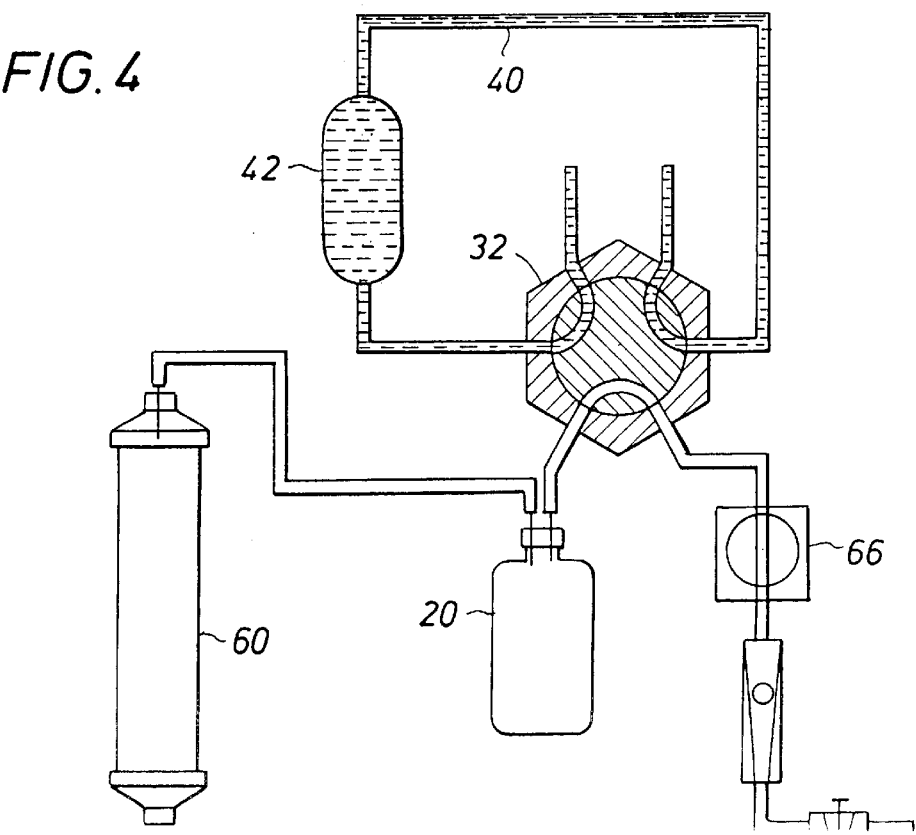

FIG. 4 of the drawings shows the valve 32 operated by rotation through 60°. In this instance, the sample loop 40 is connected with the process and the sample loop is filled. The sample loop 40 is permitted to be filled during continuous circulation for an adequate time interval to assure that the loop 40 is filled with essentially pure sample material. While this is occurring in that part of the equipment, the purge gas flow is directed through the blocking valve 66 and is then delivered into the sample container 20 and flows from the sample container 20 through the filter 60. This purges the lines which interconnect from the purge gas source through the sample container.

Figure 5:
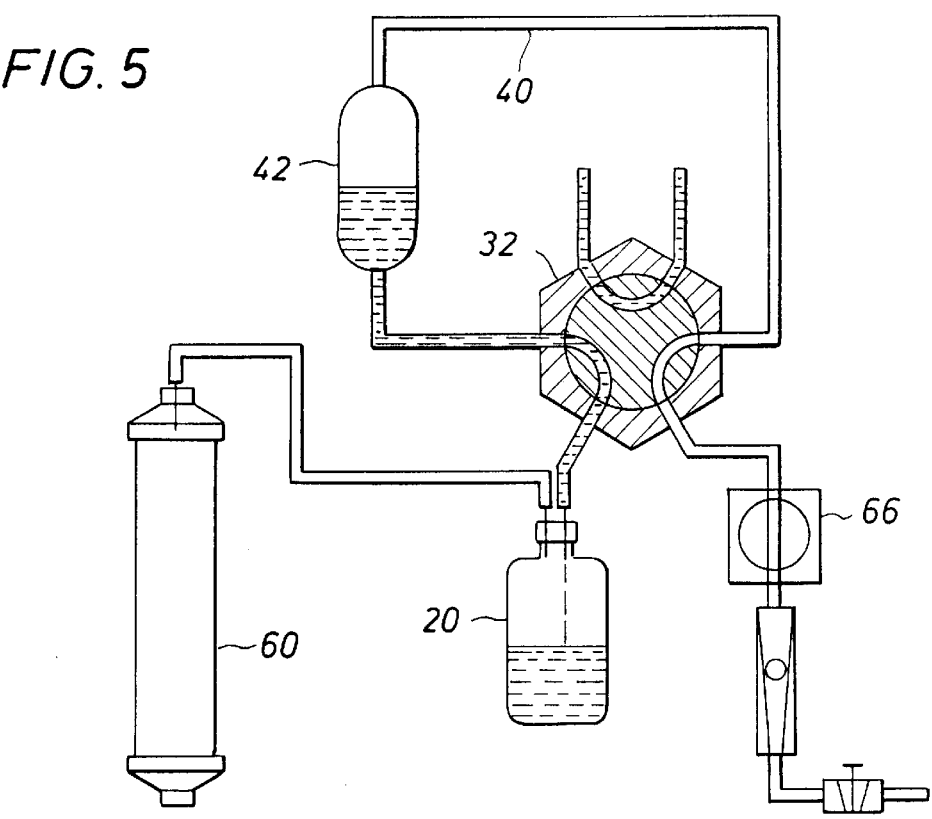

The next involves operation of the valve 32. This is shown in FIG. 5 of the drawings. After it is operated to the position shown the valve 32 is restored to the position shown in FIG. 3 of the drawings. The sample is then isolated in the sample loop 40. Recall again that this loop has a large or small capacity as required. The sample loop is then cleared by delivery of the purge gas through the blocking valve 66, the sample storage loop 40 and into the sample container 20. Delivery is continued for a sufficient interval to assure that the flow clears all the sample into the container. Any surplus is directed through the filter 60 along with the purge gas. Here, it is especially helpful to note that the sample storage loop can be changed in size. It can be as large or small as needed. It can be large or small to match the container 20. Moreover, the container 20 is filled to the desired level of the container. If the container is as large as one liter, it is readily handled. If the container is as small as one cc, it is small and is handled in a different fashion. Additional apparatus regarding the handling of the small containers will be disclosed and described. In any case, FIG. 5 shows the sequence of operations in which the sample is transferred from the sized sample loop 40 into the sample container 20.

Figure 6:
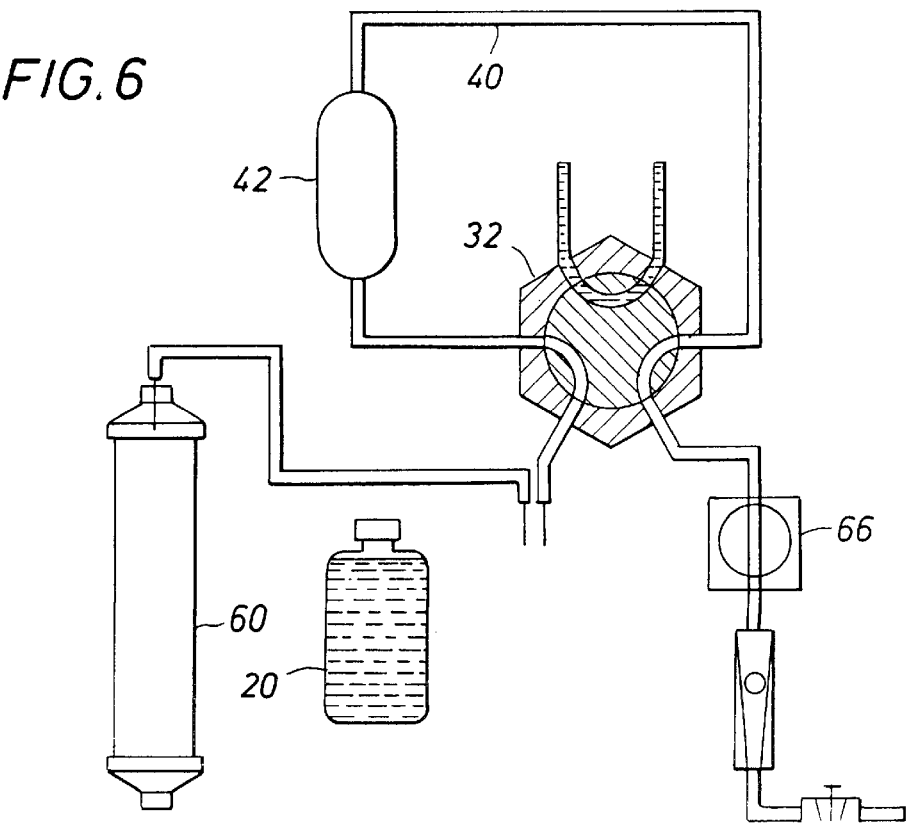

FIG. 6 of the drawings shows the last position of the equipment. At this point in time, the blocking valve 66 is closed to prevent the flow of nitrogen. The sample loop 40 has been cleared. The lines connecting with the filter 60 have also been cleared by the purge gas. The sample container 20 can then be removed from the syringe needles and a new bottle placed on the syringe needles. The process is also isolated at this moment. This enables a sample container to be placed on the syringe needles so that the equipment is restored to the operative state shown in FIG. 3. The sequence of steps is repeated beginning with the arrangement shown in FIG. 3 then to FIG. 4, filling which is accomplished in FIG. 5 and sample container removal which is then shown in FIG. 6.

FIGS. 7 AND 8 CONSIDERED JOINTLY

Attention is now directed to FIGS. 7 and 8 which show a mechanism for handling a number of duplicate sample containers. In this aspect, attention is first directed to the side view of the equipment which handles a plurality of duplicate containers. An elongate trough 70 supports a series of containers which are delivered from a container source. They traverse the trough 70. They are typically arranged so that the containers to stand erect. This enables the top end of all the containers be aligned for filling through the syringe needles. The containers are forced along the pathway defined by the trough 70. As shown in the plan view, a set of detents 72 is used to hold the last container supported by the trough. That container is forced out of the trough in a controlled fashion. In one aspect of this, the containers in the trough are pushed by a ram 74 at the left hand end of the trough in FIG. 8. When the trough is filled with sample containers, the stroke of the ram 74 is readily controlled. Moreover, a reciprocating ram 74 is preferably used wherein a connective rod 76 extends to the ram and provides reciprocating motion to the ram 74 from a double acting hydraulic or pneumatic cylinder 78. This indexes the containers 20 by the width of one container. The containers are held against accidental misregistration. The detents assure that the containers are fed singly.

Returning now to FIG. 7 of the drawings, this structure further includes a mechanism for transporting a single container. The mechanism incorporates a circular platform with a semi-circular skirt which is identified at 80. This is positioned adjacent to the end of the trough so that a single container is forced into a cradled position. It is supported beneath and on the for side. Since movement is from left to right, this assists in seating each individual container. When seated, the container is held so that it can then be forced upwardly against the syringe needles thereabove. The needles 52 and 54 are again shown in this view. They are part of the system 10 shown in FIG. 1 of the drawings. When this occurs, the cradled container is held in the uppermost position stabbed by the two syringes, and the filling operation can then occur. This requires movement of the container 20 between three positions. The first position occurs after the container has been delivered from the trough 70 and is cradled by the means 80. A hydraulic cylinder 82 is used to extend a piston rod upwardly to move the container to the installed position or the second position in this sequence of operations. After the container has been filled, the container can then be moved downwardly to a third position. That requires retraction of the extending piston rod 84. When retracted, it moves the individual container to an aligned location for marking. The location for marking positions the container 20 so that a symbol can be printed on it. This involves the operation of a time and date clock. This forms a suitable signal which is then input to an ink jet printer. Once the hydraulic cylinder has retracted to the third position, the container that had just been filled is positioned immediately opposite the ink jet printer. A suitable symbol is printed on the side of the container. As an example, the container can be marked with a bar code symbol, or other indicia of time and date. It can be directly readable or can be provided in a code form.

The time and date clock 86 provides a suitable instruction signal to the ink jet printer 88 which enables it to form the unique containers markings. When that occurs, then the container can be dumped. In one aspect of the present disclosure, a motor 90 is mechanically connected to the cylinder 82 to impart rotation. The cylinder is rotated so that the container cradled on the device is then dumped. It can be dumped into a large basket or other receptacle (not shown) for the containers 20. If this receptacle is filled in one day, and samples are taken every hour, twenty four uniquely marked containers are received in the receptacle. Even over a long weekend, as many as 48 or 72 containers can be appropriately received and stored. This is especially helpful for equipment which runs around the clock throughout most of the year. This enables the production to be measured and assayed for testing in a laboratory. Again, the performance of the system can be measured and known periodically.

In one aspect, the apparatus shown in FIGS. 7 and 8 is a system which provides multiple containers of some suitable size. Actually, the containers can be as large or small as needed. Typically, a one liter container is relatively large while a container for one cc is relatively small in diameter and typically is not very tall. It will typically measure from about 2 to about 4 cm in height. If it is unduly small, the ink jet printer 88 can print on a label which is adhesively glued to or otherwise attached to the individual container. In any event, the individual containers are tagged or labeled with a suitable code symbol to enable the sample in the container to be uniquely associated with the production flow at a particular time and on a particular day. For that reason, the system is able to provide a regular indication of time and date. This especially helps in the isolation of individual samples in a large sample lot which is periodically taken to a test laboratory.

The apparatus of FIG. 7 can be used with the structure shown in FIG. 1. In that particular instance, it may be necessary to align the sample container 20 and the transport mechanism as shown in FIG. 7 so that the sample container is properly aligned with the syringe needles 52 and 54.

The motor 34 and the timer 36 are preferably powered electrically with low voltage to reduce explosion risk. In some instances, they can be gas powered, for instance, by the purge gas flow. In that case, the risk of spark initiated explosion is further reduced. Likewise, the cylinders and motors in FIGS. 7 and 8 can be pneumatic powered.

While the foregoing is directed to the preferred embodiments, the scope is determined by the claims which follow.

I claim:

1. A method of collecting a plurality of samples from a process operating at a process pressure, comprising the steps of:
   (a) connecting a sample input line to said process and flowing a sized sample from said process through said sample input line and through a valve means and into a sized sample measuring means comprising a sized buffer tank;
   (b) filling said sized sample to a selected ambient pressure within said sized buffer tank, wherein said ambient pressure is lower than said process pressure;
   (c) delivering said sized sample from said sized buffer tank through said valve means and through a sample delivery means and into a sized sample container in a plurality of sized sample containers;
   (d) clocking and controlling the accurance of sized sample delivery with a clock, and marking said sized sample container with said clocked accurance and removing said sized sample container containing said sized sample from said sample delivery means;
   (e) forming a time dependent indicator based upon said clocking for said sized sample container so that said sized sample is uniquely identified to distinguish said sample:
   (f) purging said sized buffer tank and said valve means and said sample delivery means with purge gas after said sample delivery;
   (g) positioning another sized sample container from said plurality of sized sample containers to receive another sized sample from said sample delivery means; and
   (h) repeating steps (b) through (g).

2. The method of claim 1 wherein:
   (a) said plurality of said sized sample containers is aligned serially along a guide surface pathway;
   (b) positioning said pathway cooperatively to enable each of said sample receiving container to move sequentially into operative connection with respect to said sample delivery means;
   (c) delivering the sized sample from said sample delivery means responsive to a gas drive for delivery of said sized sample to said sized sample container; and
   (d) wherein said time of said sized sample delivery of each said sized sample container is measured and controlled by said clock.

3. The method of claim 2 wherein said gas drive is supplied to said sized buffer tank through said valve means to initiate said delivery of said sized sample to said sized sample container.

4. The method of claim 3 wherein said valve means is a multiport valve with multiple settings, and said sized buffer tank is hydraulically isolated from said process when said valve is set in a first position.

5. The method of claim 3 wherein said valve means is a multiport valve with multiple settings, and said sized buffer tank is hydraulically connected to said process to fill said sized buffer tank with said sized sample when said valve is set in a second position.

6. The method of claim 3 wherein said valve means is a multiport valve with multiple settings, and said sized buffer tank is hydraulically connected to said gas drive and said sized sample container when said valve is set in a third position, and said sized sample is delivered from said sized buffer tank and through said valve and into said sized sample container by said gas drive.

7. The method of claim 4 wherein said sized buffer tank and said valve means and said sample delivery means are purged with said purge gas from said gas drive when said valve is set in said first position.

8. The method of claim 1 wherein:
   (a) said sample delivery means comprises a pair of syringe needles;
   (b) said sized sample container comprises a septum; and
   (c) said pair of syringe needles punctures said septum and said sized sample is delivered to said sized sample container through a first needle of said pair of said syringe needles.

9. The method of claim 8 wherein said purge gas is flowed through said valve means and through said first syringe needle, and waste products are flowed from said sized sample container and into a filter container through a second needle of said pair of syringe needles.

10. The method of claim 3 wherein said valve means is a multiport valve with multiple settings, and said valve moves between said multiple settings as determined by a motor.

11. The method of claim 1 wherein said sized sample container is sized to receive and store a single said sized sample.

12. The method of claim 11 wherein each of said plurality of sized sample containers is filled with said single sized sample in timed sequence by a means moving each of said sized sample containers into operative connection with respect to said sample delivery means.

* * * * *